US008798702B2

(12) United States Patent
Trumble

(10) Patent No.: US 8,798,702 B2
(45) Date of Patent: Aug. 5, 2014

(54) MULTIPLEXED PHOTODETECTOR ARRAY FOR OPTICAL MEDICAL SENSORS

(75) Inventor: David Trumble, Boulder, CO (US)

(73) Assignee: Covidien LP, Mansfield, MA (US)

( * ) Notice: Subject to any disclaimer, the term of this patent is extended or adjusted under 35 U.S.C. 154(b) by 672 days.

(21) Appl. No.: 13/077,105

(22) Filed: Mar. 31, 2011

(65) Prior Publication Data

US 2012/0253153 A1 Oct. 4, 2012

(51) Int. Cl.
*A61B 5/1455* (2006.01)

(52) U.S. Cl.
USPC .......................................... 600/323; 600/310

(58) Field of Classification Search
USPC .................. 600/310, 322, 323, 336
See application file for complete search history.

(56) References Cited

U.S. PATENT DOCUMENTS

| 5,817,007 A * | 10/1998 | Fodgaard et al. ............ 600/322 |
|---|---|---|
| 2006/0287589 A1 | 12/2006 | Wobermin et al. |
| 2007/0060807 A1 | 3/2007 | Oishi |
| 2007/0078309 A1 | 4/2007 | Matlock |
| 2007/0100218 A1 | 5/2007 | Sweitzer et al. |
| 2007/0100219 A1 | 5/2007 | Sweitzer et al. |
| 2007/0129613 A1 | 6/2007 | Rochester et al. |
| 2008/0106792 A1 | 5/2008 | Lash et al. |
| 2008/0108886 A1 | 5/2008 | Lash et al. |
| 2009/0275841 A1 | 11/2009 | Melendez et al. |
| 2009/0326346 A1 | 12/2009 | Kracker et al. |
| 2010/0026995 A1 | 2/2010 | Merritt et al. |
| 2010/0030040 A1 | 2/2010 | Poeze et al. |
| 2010/0331640 A1 | 12/2010 | Medina |

FOREIGN PATENT DOCUMENTS

| FR | 2685865 | 7/1993 |
|---|---|---|
| JP | 4038280 | 9/1998 |
| JP | 28119026 | 11/2006 |
| WO | 9309711 | 5/1993 |
| WO | 9502358 | 1/1995 |

OTHER PUBLICATIONS

Crilly, Paul B., et al.; "An Integrated Pulse Oximeter System for Telemedicine Applications," IEEE Instrumentation and Measurement Technology Conference, Ottawa, Canada; May 19-21, 1997; pp. 102-104.

(Continued)

*Primary Examiner* — Eric Winakur
(74) *Attorney, Agent, or Firm* — Fletcher Yoder PC

(57) ABSTRACT

The present disclosure relates generally to medical devices and, more particularly, to optical medical sensors used for sensing physiological characteristics of a patient. In one embodiment, a system includes a physiological sensor having a photodetector array with a plurality of photodetectors configured to receive light from patient tissue. The physiological sensor also includes a multiplexor configured select and output a signal from the photodetector array. The physiological sensor may also include a signal analyzer configured to determine the signal quality for each of the output signals of the photodetector array and select an output signal, based on the signal quality determination, for the calculation of a physiological parameter of the patient. In another embodiment, a system includes a pulse oximetry sensor having a multiplexed array of photodetectors configured to receive light from patient tissue. The system also includes a pulse oximetry monitor having a multiplexor driver to control the multiplexed array of photodetectors as well as a processor configured to control the multiplexor driver and receive the output signals from the array of photodetectors. The processor is also configured to determine the signal quality of each of the output signals from the array of photodetectors, select an output signal based on the signal quality determination, and use the selected signal to calculate a physiological parameter of a patient.

17 Claims, 7 Drawing Sheets

(56) References Cited

OTHER PUBLICATIONS

Rhee, Sokwoo, et al.; "The Ring Sensor: a New Ambulatory Wearable Sensor for Twenty-Four Hour Patient Monitoring," Proceedings of the 20th annual International Conference of the IEEE Engineering in Medicine and Biology Society, 1998, vol. 20, No. 4, pp. 1906-1919.

Yang, Boo-Ho, et al.; "A Twenty-Four Hour Tele-Nursing System Using a Ring Sensor," Proceedings of the 1998 IEEE International Conference on Robotics & Automation, Leaven, Belgium, May 1998; pp. 387-392.

Lutter, N., et al.; "Comparison of Different Evaluation Methods for a Multi-wavelength Pulse Oximeter," Biomedizinische Technik, vol. 43, (1998).

Ferrell, T.L., et al.; "Medical Telesensors," SPIE, vol. 3253, pp. 193-198 (1998).

Ikeda, Kenji, et al.; "Improvement of Photo-Electric Plethysmograph Applying Newly Developed Opto-Electronic Devices," IEEE Tencon, pp. 1109-1112 (1999).

Yang, Boo-Ho, et al.; "Development of the ring sensor for healthcare automation," Robotics and Autonomous Systems, vol. 30, pp. 273-281 (2000).

Rhee, Sokwoo, et al.; "Artifact-Resistant, Power-Efficient Design of Finger-Ring Plethysmographic Sensor—Part I: Design and Analysis," Proceedings of the 22nd Annual EMBS International Conference, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," Proceedings of the 22nd Annual EMBS International Conference, Chicago, Illinois; Jul. 23-28, 2000; pp. 2796.

Cubeddu, Rinaldo, et al.; "Portable 8-channel time-resolved optical imager for functional studies of biological tissues," Photon Migration, Optical Coherence Tomography, and Microscopy, Proceedings of SPIE, vol. 4431, pp. 260-265 (2001).

Rhee, Sokwoo, et al.; "Artifact-Resistant, Power-Efficient Design of Finger-Ring Plethysmographic Sensor," IEEE Transactions on Biomedical Engineering, vol. 48, No. 7, pp. 795-805 (Jul. 2001).

Lopez-Silva, Sonnia Maria Lopez, et al.; "NIR transmittance pulse oximetry system with laser diodes," Clinical Diagnostic Systems, Proceedings of SPIE, vol. 4255, pp. 80-87 (2001).

Maletras, Francois-Xavier, et al.; "Construction and calibration of a new design of Fiber Optic Respiratory Plethysmograph (FORP)," Optomechanical Design and Engineering, Proceedings of SPIE, vol. 4444, pp. 285-293 (2001).

Liu, Ying, et al.; "Sensor design of new type reflectance pulse oximetry," Optics in Health Care and Biomedical Optics: Diagnostics and Treatment, Proceedings of SPIE, vol. 4916, pp. 98-102 (2002).

Shaltis, Phillip, et al.; "Implementation and Validation of a Power-Efficient, High-Speed Modulation Design for Wireless Oxygen Saturation Measurement Systems," IEEE, pp. 193-194 (2002).

Warren, Steve, et al.; "Wearable Sensors and Component-Based Design for Home Health Care," Proceedings of the Second Joint EMBS/BMES Conference, Houston, Texas; Oct. 23-26, 2002; pp. 1871-1872.

Lopez-Silva, Sonnia Maria Lopez, et al.; "Near-infrared transmittance pulse oximetry with laser diodes," Journal of Biomedical Optics, vol. 8, No. 3, pp. 525-533 (Jul. 2003).

Mendelson, Y., et al.; "Measurement Site and Photodetector Size Considerations in Optimizing Power Consumption of a Wearable Reflectance Pulse Oximeter," Proceedings of the 25th Annual International conference of the IEEE EMBS, Cancun, Mexico, Sep. 17-21, 2003.

Lebak, J.W., et al.; "Implementation of a Standards-Based Pulse Oximeter on a Wearable, Embedded Platform," Proceeding of the 25th Annual International Conference of the IEEE EMBS, Cancun, Mexico, Sep. 17-21, 2003; pp. 3196-3198.

Nagl, L., et al.; "Wearable Sensor System for Wireless State-of-Health Determination in Cattle," Proceeding of the 25th Annual International Conference of the IEEE EMBS, Cancun, Mexico, Sep. 17-21, 2003; pp. 3012-3015.

Pujary, C., et al.; "Photodetector Size Considerations in the Design of a Noninvasive Reflectance Pulse Oximeter for Telemedicine Applications," IEEE, pp. 148-149 (2003).

Wendelken, Suzanne, et al.; "The Feasibility of Using a Forehead Reflectance Pulse Oximeter for Automated Remote Triage," IEEE, pp. 180-181 (2004).

Lopez-Silva, S.M., et al.; "Transmittance Photoplethysmography and Pulse Oximetry With Near Infrared Laser Diodes," IMTC 2004—Instrumentation and Measurement Technology Conference, Como, Italy, May 18-20, 2004; pp. 718-723.

Johnston, W.S., et al.; "Extracting Breathing Rate Infromation from a Wearable Reflectance Pulse Oximeter Sensor," Proceedings of the 26th Annual International conference of the IEEE EMBS, San Francisco, California; Sep. 1-5, 2004; pp. 5388-5391.

Odagiri, Y.; "Pulse Wave Measuring Device," Micromechatronics, vol. 42, No. 3, pp. 6-11 (undated) (Article in Japanese—contains English summary of article).

* cited by examiner

MULTIPLEXED PHOTODETECTOR ARRAY FOR OPTICAL MEDICAL SENSORS

BACKGROUND

The present disclosure relates generally to medical devices and, more particularly, to optical medical sensors used for sensing physiological characteristics of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors frequently desire to monitor certain physiological characteristics of their patients. Accordingly, a wide variety of devices have been developed for monitoring many such physiological characteristics. These devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to non-invasively measure various blood flow characteristics, such as the blood-oxygen saturation of hemoglobin in arterial blood, the volume of individual blood pulsations supplying patient tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize an emitter to transmit light through a patient's tissue, toward a detector that photoelectrically detects the amount of light that has been lost due to absorption and/or scattering by the tissue. Based upon the amount of light absorbed or scattered, one or more of the above physiological characteristics may be calculated. Light passed through the tissue is typically selected to be of one or more wavelengths that may be absorbed or scattered by the patient's blood to a degree that correlates with the amount of a particular blood constituent present in the blood. Therefore, the amount of light absorbed and/or scattered may then be used to estimate the amount of blood constituent in the tissue using various algorithms.

Pulse oximeter sensors typically are placed in a certain position on a patient. For the sensor to operate properly, this position must be maintained. Small changes in the conformation of the sensor may cause the optical components to lose their contact with the skin, resulting in changes to the emitted and/or detected light, which in turn may lead to signal artifacts. Additionally, the photodetector should be oriented in such a way to receive a clear signal from the emitter despite potential transmission barriers (e.g., bone) in the tissue. Since it may prove difficult to constantly maintain emitter and photodetector positioning for a sensor attached to a moving patient, it may be beneficial to employ multiple photodetectors and/or emitters on a single sensor such that the probability of obtaining a good physiological measurement at a given time may be improved.

However, while using an array of photodetectors may address the aforementioned issues, it also introduces new challenges. For example, if every photodetector in the photodetector array were to possess a dedicated line to the monitor, the cable required to couple a sensor having a large number of photodetectors to a monitor would quickly become impractical, especially since the size and weight of the cable might tend to dislodge the sensor from its position on the patient's body. Additionally, the manufacturing cost and the likelihood of manufacturing defects would also be expected to increase with the increasing number of communication lines that would be coupled to the sensor, traverse the length of the cable, and be properly coupled to the monitor for the system to be operational.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
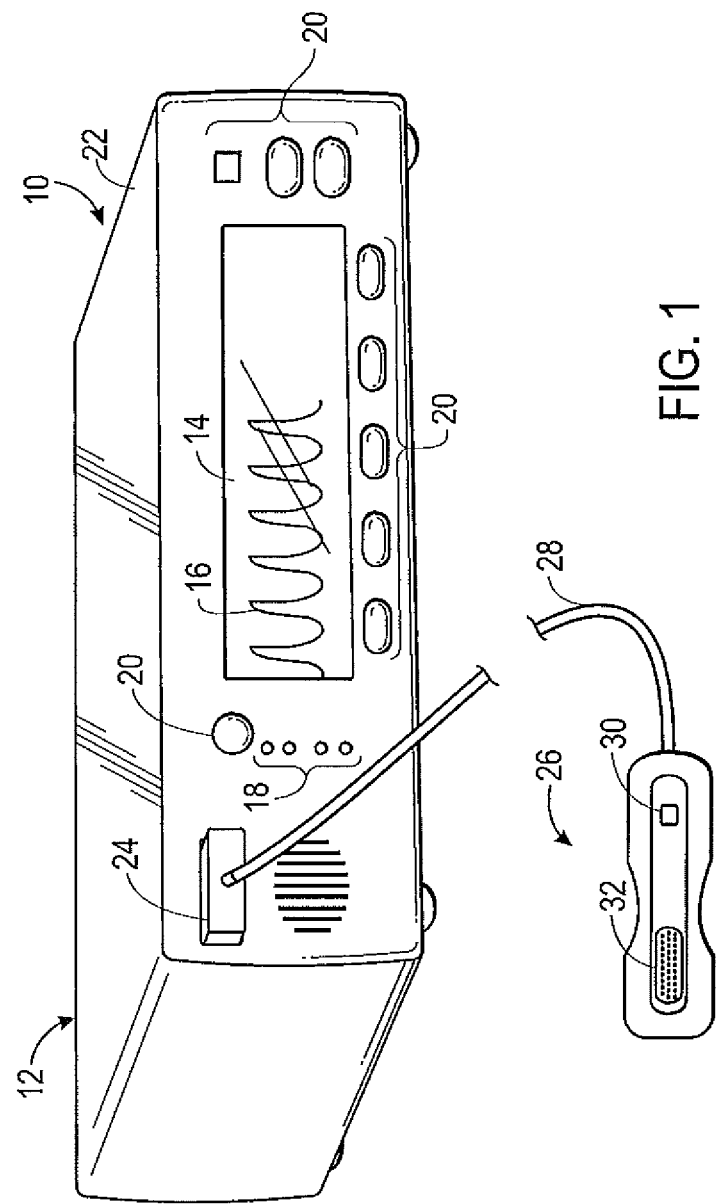
FIG. 1 illustrates a perspective view of a pulse oximeter, in accordance with an embodiment of the present disclosure.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Medical sensors (e.g., pulse oximetry sensors) may be placed on a patient in a location that is normally perfused with arterial blood to facilitate measurement of the desired blood characteristics, such as arterial oxygen saturation measurement ($SpO_2$). Accordingly, present embodiments relate to non-invasively measuring physiologic parameters in a patient by emitting light into a patient's tissue with light emitters (e.g., light emitting diodes) and photoelectrically detecting the light after it has passed through the patient's tissue. More specifically, present embodiments are directed toward increasing the effective area of photodetectors in a pulse oximetry sensor in an effective and efficient manner using one or more arrays of photodetectors. Utilization of photodetector arrays in pulse oximetry sensors may allow for increased efficiency of the overall pulse oximetry system by allowing the sensor to detect light at multiple locations. Thus, if a path between an emitter and a photodetector is blocked by tissue, bone, or other constituents, paths between the emitter and other photodetectors in an array may be used to transmit light signals. Accordingly, a photodetector array may be scanned to determine which individual photodetectors in the array are receiving the strongest light transmission and/or producing the best quality electrical signal. Then, this optimal signal from the photodetector array may be utilized by the monitor to calculate physiological parameters of a patient. Additionally, one or more photodetector arrays may be employed to measure different wavelengths of light being passed through the patient's tissue, affording a single sensor the ability to simultaneously assess multiple physiological characteristics of a patient.

However, utilizing a photodetector array within a medical sensor introduces a certain amount of complexity into the system. For example, it may become cumbersome for every photodetector in a photodetector array to have a dedicated communication line (i.e. a wired or wireless channel) to the monitor so that the monitor can receive signals from the photodetector array. As such, present embodiments relate to using a multiplexed array of photodetectors to minimize the number of communication lines required for the monitor to interface with the photodetector array on the sensor. Indeed, some sensor embodiments may also include multiplexor control and signal selection circuitry configured to select and output only the best quality signal from a photodetector array. Therefore, an embodiment of a sensor having a multiplexed photodetector array may not use any additional communication lines between the sensor and monitor than a single photodetector sensor.

Turning to FIG. 1, a perspective view of a medical device is illustrated in accordance with an embodiment. The medical device may be a pulse oximeter 10. The pulse oximeter 10 may include a monitor 12, such as those available from Nellcor Puritan Bennett LLC. The monitor 12 may be configured to display calculated parameters on a display 14. As illustrated, the display 14 may be integrated into the monitor 12. However, the monitor 12 may be configured to provide data via a port (not shown) to a display or to another monitoring device not integrated with the monitor 12. The display 14 may be configured to display computed physiological data including, for example, an oxygen saturation percentage, a pulse rate, and/or a plethysmographic waveform 16. As is known in the art, the oxygen saturation percentage may be a functional arterial hemoglobin oxygen saturation measurement in units of percentage $SpO_2$, while the pulse rate may indicate a patient's pulse rate in beats per minute. The monitor 12 may also display information related to alarms, monitor settings, and/or signal quality via indicator lights 18. To facilitate user input, the monitor 12 may include a plurality of control inputs 20. The control inputs 20 may include fixed function keys, programmable function keys, a touch screen, and soft keys. The control inputs may allow the user to adjust operational parameters of the pulse oximeter 10, such as calibrating sensors or adjusting coefficients used in the calculation of the patient's physiological characteristics. The monitor 12 may also include a casing 22 that may aid in the protection of the internal elements of the monitor 12 from damage.

The monitor 12 may further include a sensor port 24. The monitor 12 may allow for connection to an external sensor 26 via cable 28, which connects to the sensor port 24. Alternatively, a wireless transmission device or the like may be utilized instead of (or in addition to) the cable 24. Furthermore, the sensor 26 may be of a disposable or a non-disposable type. The photodetector array may also be placed on a flexible substrate so as to allow the sensor to be more form fitting. The sensor 26 includes one or more emitters 30 configured to emit light of one or more wavelengths through a portion of a patient's tissue and toward an array of photodetectors 32, which in turn detect light passing through, reflected or fluoresced by the patient's tissue. The pulse oximetry monitor 12 may be configured to calculate physiological parameters received from the sensor 26 relating to this light detection. For example, the sensor 26 may obtain readings from a patient, which can be used by the monitor to calculate certain physiological characteristics, such as the blood-oxygen saturation of hemoglobin in arterial blood, the volume of individual blood pulsations supplying the tissue, and/or the rate of blood pulsations corresponding to each heartbeat of a patient.

Figure 2:
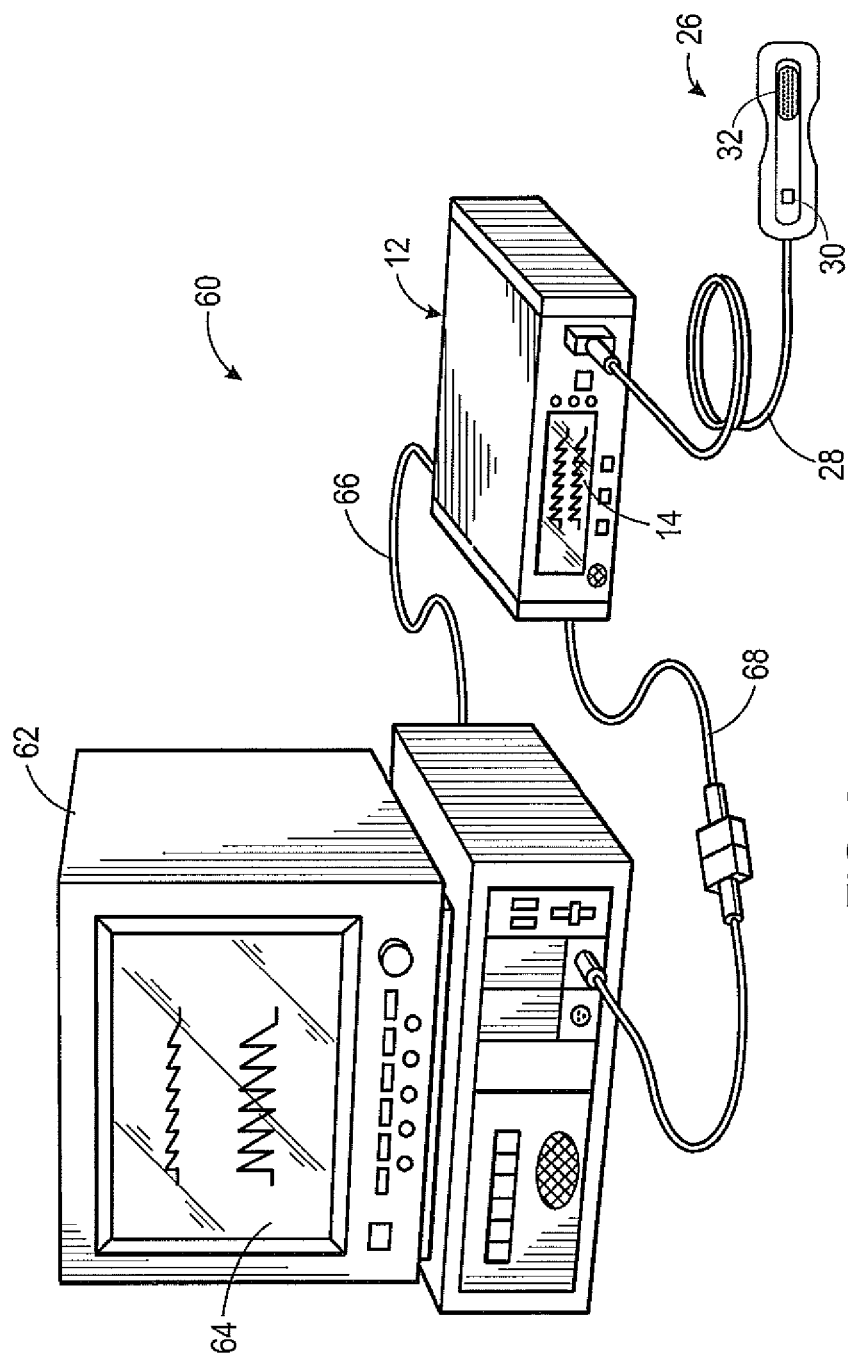
FIG. 2 illustrates a perspective view of pulse oximeter as part of a multiparameter monitoring system, in accordance with an embodiment of the present disclosure.

In certain circumstances, it may be useful for medical professional to have various physiological parameters of the patient collected and displayed by a single monitor. In the embodiment illustrated in FIG. 2, such functionality may be provided by a multi-parameter patient monitoring system 60. The multi-parameter patient monitoring system 60 includes a multi-parameter patient monitor 62 that may include a computer or similar processing-relating equipment. The multi-parameter patient monitor 62 is generally configured to calculate physiological parameters and to provide a display 64 for information from the pulse oximeter 10 as well as from other medical monitoring devices or systems. In the present context, the multi-parameter patient monitor 62 may allow a user to address the pulse oximetry monitor 12, for example, to adjust operational parameters or manage alerts. Additionally, the central display 64 may allow the user to, for example, view current settings, view real-time frequency spectra, view alarms, etc. for the pulse oximeter 10 or other connected medical monitoring devices and systems. The pulse oximetry monitor 12 may be communicatively coupled to the multi-parameter patient monitor 62 via a cable 66 or 68 and coupled to a sensor input port or a digital communications port, respectively. In addition, the pulse oximetry monitor 12 and/or the multi-parameter patient monitor 62 may be connected to a network to enable the sharing of information with servers or other workstations.

In some embodiments, a sensor having a multiplexed photodetector array may be controlled by components (e.g., a multiplexor driver working in conjunction with a processor) located in the monitor. Such embodiments may be advantageous in terms of manufacturing cost given that some embodiments of sensors may be disposable, and as such, having the multiplexor control circuitry as part of the monitor allows for a recycling of this circuitry, thereby limiting waste.

Figure 3:
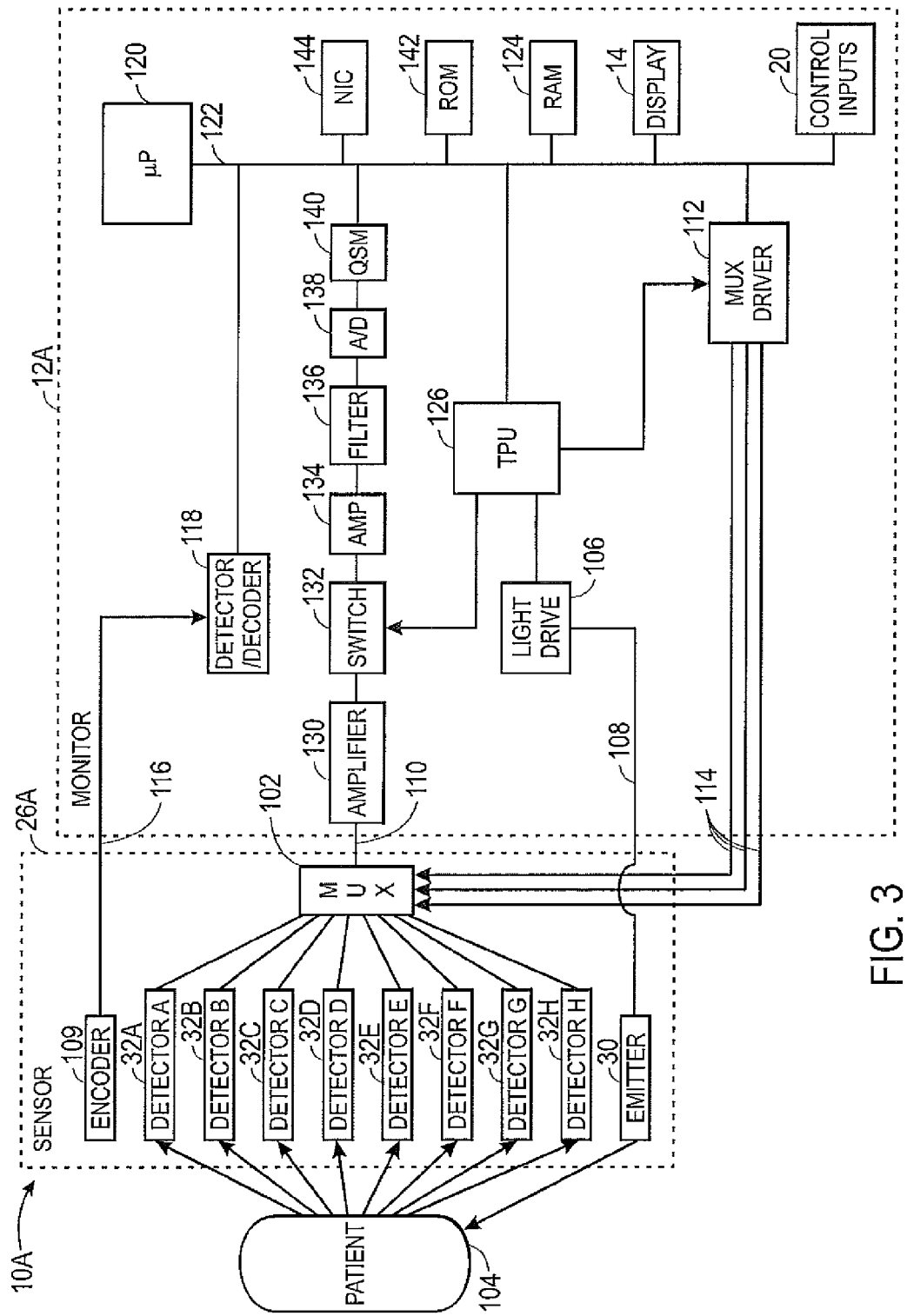
FIG. 3 illustrates a simplified block diagram of a pulse oximeter, wherein the multiplexed array of photodetectors is controlled by a multiplexor driver in the monitor, in accordance with an embodiment of the present disclosure.

For example, turning to FIG. 3, a simplified block diagram of a pulse oximeter 10A is illustrated in which the multiplexor control circuitry is located in the monitor. Specifically, certain components of the sensor 26A and the monitor 12A are illustrated in FIG. 3. The sensor 26A may include an emitter 30, and an array of photodetectors 32A-H individually attached to a multiplexor 102. An emitter 30 may be capable of emitting light into the tissue of a patient 104 to determine the physiological characteristics of the patient 104. The light emitted by an emitter 30 may be used to measure, for example, blood oxygenation levels, pulse rate, water fractions, hematocrit, or other physiologic parameters of the patient 104. It should be understood that, as used herein, the term "light" may refer to one or more of ultrasound, radio, microwave, millimeter wave, infrared, visible, ultraviolet, gamma-ray or X-ray electromagnetic radiation, and may also include any wavelength within the radio, microwave, infrared, visible, ultraviolet, or X-ray spectra, and that any suitable wavelength of light may be appropriate for use with the present disclosure.

In one embodiment, the emitter 30 may be capable of emitting multiple wavelengths of light. For example, for pulse oximeter measurements, an emitter 30 may emit RED and infrared (IR) light, where the RED light may have a wavelength of about 600 to 700 nm, and the IR light may have a wavelength of about 800 to 1000 nm. In another embodiment, more than one emitter 30 may be included on the sensor 26A, and each emitter 30 may only produce a single wavelength of light (e.g., one emitter emits RED while another emitter only emits IR). In an embodiment with multiple emitters 30, more than one emitter may also be activated to produce the same wavelength of light, increasing the total intensity of light at that wavelength being emitted by the sensor 26A. The emitter 30 may be controlled by the light drive 106 of the monitor 12A via the emitter line 108. In another embodiment, the light may be produced by the light drive 106 inside the monitor 12A and subsequently transmitted to the emitter 30, for example, using one or more fiber-optic cables as the emitter line 108.

Additionally, the sensor 26A may include an encoder 109, which may contain information about the sensor 26A. Such information may include the sensor type (e.g., whether the sensor is intended for placement on a forehead, digit, earlobe, etc.), the number and organization of photodetectors 32 and emitters 30 present on the sensor, the wavelengths of light emitted by the emitter 30, etc. The information provided by the encoder 109 may be supplied to the monitor 12A via the encoder signal line 116 and may indicate to the monitor 12A how to interface with the sensor to control sensor 26A operation and exchange data. For example, the encoder 109 may supply the monitor 12A with information regarding the control and data lines (i.e. lines 108, 110, 114, and 116) between the monitor 12A and the sensor 26A as well as the types and ranges of signals may be transmitted via these communication lines during operation. The encoder 109 may also, for example, indicate to the monitor 12A that the sensor 26A has a multiplexed array of photodetectors 32 and that the select lines 114 may be utilized to control the photodetector array 32. The encoder 109 may also provide information to allow the monitor 12A to select appropriate algorithms and/or calibration coefficients for calculating the physiological characteristics of the patient 104. The encoder 109 may, for instance, be implemented as a memory on which the described sensor information may be stored. In one embodiment, the data or signal from the encoder 109 may be decoded by a detector/decoder 118 in the monitor 12A, and the detector/decoder 118 may be coupled to the processor 120 via the internal bus 122 of the monitor 12A.

In the depicted embodiment of FIG. 3, the sensor 26A may possess an array of photodetectors 32 capable of detecting light at various intensities and wavelengths and converting the received light to an electrical signal. In operation, light enters a photodetector (e.g., any of 32A-H) after passing through the tissue of the patient 104. For example, a photodetector (e.g., any of 32A-H) may convert light at a given intensity, which may be directly related to the absorbance and/or reflectance of light in the tissue of the patient 104, into an electrical signal. That is, when more light of a certain wavelength is absorbed, reflected, or otherwise scattered, less light of that wavelength is typically received back from the tissue by a photodetector (e.g., any of 32A-H).

Rather than have every individual photodetector in the photodetector array 32 have a dedicated communication line to the monitor 12A, each photodetector 32A-H may instead be connected to a multiplexor 102 whose output is, in turn, coupled to the signal input line 110 of monitor 12A. In the depicted embodiment, the multiplexor 102 may be coupled to a multiplexor driver 112 (located in the monitor 12A) by one or more select lines 114 (e.g., control lines). As would be appreciated by one of ordinary skill in the art, the maximum number of multiplexed photodetectors that may be controlled by N select lines 114 typically equals two raised to the $N^{th}$ power (i.e. $2^N$). For example, a photodetector array 32 having eight multiplexed photodetectors (e.g., 32A-H) may be controlled by a multiplexor driver 112 via three select lines 114, and the multiplexor driver 112 may access each of the eight photodetectors behind the multiplexor 102 by transmitting various combinations of signals to the multiplexor 102 on the three select lines 114. Similarly, a multiplexor driver 112 may control a photodetector array 32 having nine to sixteen multiplexed photodetectors via four select lines 114. By sending signals to the multiplexor 102 via the select lines 114, the multiplexor driver 112 may instruct the multiplexor 102 to select a particular photodetector (e.g., photodetector 32A), causing the multiplexor 102 to send the output signal from the selected photodetector to the monitor 12A via the signal input line 110, allowing the patient's physiological characteristics to be calculated based (at least in part) on the absorption or scattering of light in the tissue of the patient 104.

The monitor 12A may include one or more processors 120 coupled to an internal bus 122. The processor 120 may be coupled to the multiplexor driver 112 via the internal bus 122. This allows the processor 120 to control the multiplexor driver 112, which in turn controls the multiplexor 102, as described above. Random access memory (RAM) 124 and a display 14 may also be attached to the internal bus 122. Additionally, a time processing unit (TPU) 126 may also be connected to the bus and may provide timing control signals to light drive circuitry 106 that may control the emitter 30 as described above. The light drive 106 may, for example, use a timing control signal from the TPU 126 to time the activation of an emitter 30 or different light sources (e.g., LEDs) within an emitter 30. The TPU 126 may also provide a timing control signal to the multiplexor driver 112 to time the switching of the multiplexor 102 relative to the emissions of the emitter 30, as discussed in greater detail below. The TPU 126 may also control the gating-in of signals from the sensor 26A (via the signal input line 110) through an amplifier 130 and a switching circuit 132. The incoming signals from the sensor may be sampled at specific times that may be correlated (at least in part) with the activities of the emitter 30. The signal received from the sensor 26A may subsequently be passed through an amplifier 134, a low pass filter 136, and an analog-to-digital converter 138 for amplifying, filtering, and digitizing the electrical signals the from the sensor 26A. The digital data may then be stored in a queued serial module (QSM) 140, for later downloading to RAM 124 as the QSM 140 fills up. In an embodiment, there may be multiple parallel paths for separate amplifiers, filters, and A/D converters for multiple light wavelengths or spectra received. The control inputs 20 may also be coupled to the internal bus 122 of the monitor 12A such that monitor parameters set or adjusted using the control inputs 20 may be applied in the operation of the pulse oximeter 10A. Additionally, some embodiments of the monitor 12A may also include a network interface card 144, wired or wireless, that may interface with the internal bus 122 of the monitor 12A and allow the transmission of data and/or control signals between a computer network and the monitor 12A.

In an embodiment, based at least in part upon the received signals corresponding to the light received by the photodetector array 32, the processor 120 may calculate, for example, the oxygen saturation of the patient 104 using various algorithms. These algorithms may use coefficients, which may be empirically determined. For example, algorithms relating to the distance between the emitter 30 and photodetector array 32 elements may be stored in the monitor (e.g., in ROM 142) or in the sensor (e.g., in the encoder 109) and accessed and operated according to processor 120 instructions. The processor 120 may also be utilized to scan each photodetector in the photodetector array 32 by signaling the multiplexor driver 112 to cycle through the photodetectors 32A-C, allowing the processor 120 to access the quality of the signal provided by each photodetector 32A-C. Since the multiplexor driver 112 is coupled to the TPU 126, the selection of a particular photodetector may be timed relative to the activation of an emitter 30 and/or the emission of a particular wavelength of light (e.g., RED or IR light). For example, the multiplexor 112 may cycle through the entire photodetector array 32 while only RED light is being provided by the emitter 30, and then cycle through the entire photodetector array again after the TPU 126 and the light drive 106 have collaborated to switch the emitter 30 to produce IR light. Alternatively, the multiplexor driver 112 may select a particular photodetector (e.g., photodetector 32A) and remain with that photodetector selected until the emitter 30 has cycled through all emittable wavelengths. The processor 120 may rely upon methods such as those described in FIGS. 5a-b when scanning the signals from the photodetector array 32 for the optimal signal, as will be described in greater detail below.

Figure 4:
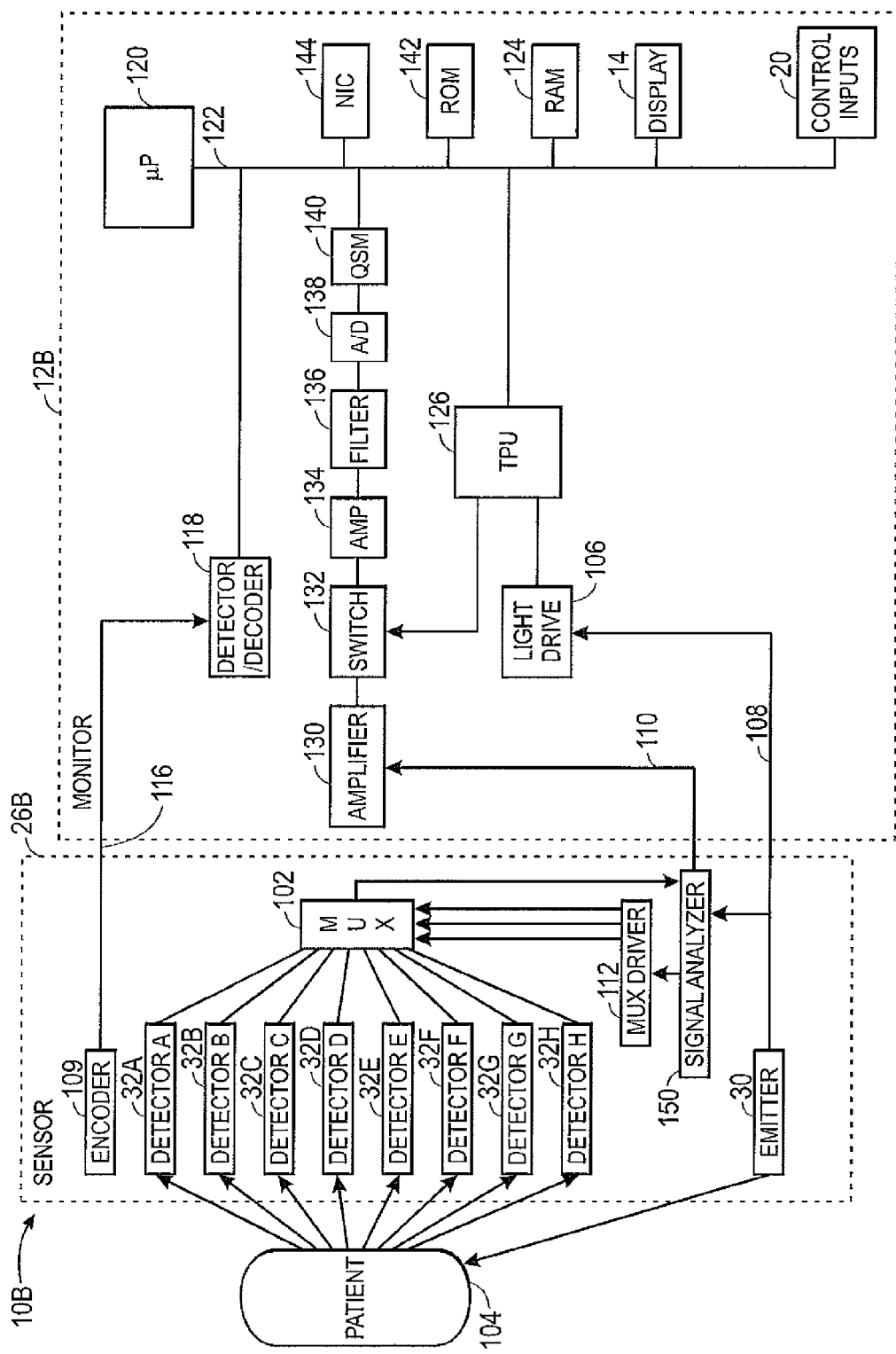
FIG. 4 illustrates a simplified block diagram of another pulse oximeter, wherein the multiplexed array of photodetectors is controlled by a multiplexor driver and signal analyzer in the sensor, in accordance with an embodiment of the present disclosure.

In some pulse oximeter embodiments, the multiplexor control circuitry may be located within the sensor 26 rather than the monitor 12. While such embodiments may not share the aforementioned manufacturing cost advantages gained by having the multiplexor control circuitry in the monitor 12, including the control circuitry in the sensor 26 may allow for greater flexibility in terms of which monitors 12 may be used with the multiplexed sensor 26, and it may also provide a further reduction in the number of communication lines used between the sensor 26 and monitor 12. For example, by locating the multiplexor control circuitry on the sensor, a monitor may not require any additional hardware, software, or communication lines to operate a multiplexed sensor than to operate a single photodetector sensor. Further, some disposable sensor 26 embodiments may implement multiplexor control circuitry that is removably attached such that it may be removed from the sensor 26 prior to sensor 26 disposal and may be attached to (i.e. recycled in) subsequent sensors 26. Turning to FIG. 4, a simplified block diagram of an embodiment of a pulse oximeter 10B is illustrated in which the multiplexor control circuitry is located within the sensor. Similar to the embodiment of FIG. 3, the sensor 26B of the embodiment of FIG. 4 may include an encoder 109, an emitter 30, and an array of photodetectors 32A-H individually attached to a multiplexor 102. Similarly, the monitor 12B may include the components included in monitor 12A (e.g., a processor 120, RAM 124, ROM 142, etc.), minus the multiplexor driver 112.

In the embodiment of FIG. 4, the multiplexor driver 112 is located on the sensor 26B rather than the monitor 12B. Additionally, the sensor 26B in the embodiment of FIG. 4 may possess a signal analyzer 150, which may be attached to the output of the multiplexor 102 and to the input of the multiplexor driver 112. The signal analyzer 150 may include a programmable logic controller (PLC), current or voltage comparison units, an analog-to-digital converter, a digital signal processor (DSP), a time processing unit (TPU), and other similar electronic circuitry. The electronic circuitry may be implemented using common CMOS technology and techniques, or alternatively using, for example, organic electronic elements to yield enhanced flexibility. The role of the signal analyzer 150 is to signal the multiplexor driver 112 to cycle through the photodetectors (e.g., 32A-H) and measure the signal that each photodetector is producing. The signal analyzer selects the optimal signal from the photodetector array 32, for example, using a method similar to those described by FIGS. 5a-b, as discussed in greater detail below. In an embodiment, the signal analyzer 150 may also be connected to the emitter line 108 to determine the state of the emitter 30 (i.e. which emitter 30, if any, is active and what wavelength is being emitted). As such, the signal analyzer 150 may determine an optimal photodetector signal for each wavelength emitted by the emitter 30. For example, photodetector 32A may possess a superior signal when the emitter 30 is emitting RED light, while photodetector 32B may afford an optimal signal when the emitter 30 is emitting IR light. Once the optimal signal has been determined, the signal is output from the signal analyzer 150 and transmitted to the monitor 12B via the signal input line 110. In some embodiments, the signal analyzer 150 may seamlessly manage the photodetector array and provide the monitor 12B with a single, optimal signal, allowing the monitor 12B to effectively treat the sensor 26B as if it were a simple, single-photodetector sensor. In such embodiments, the signal analyzer 150 may adjust or modify the signal of the selected photodetector before it is transmitted to the monitor 12B (e.g., to account for the relative positioning of the emitter 30 and the selected photodetector).

Figure 5A:
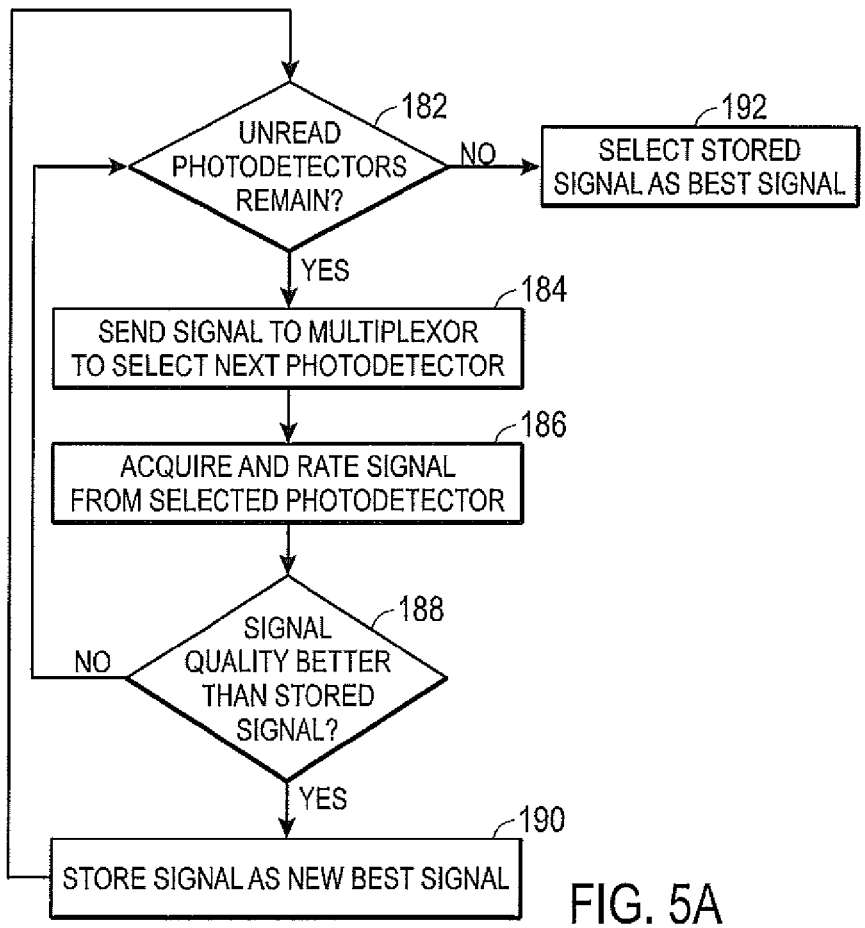
FIG. 5a is a block diagram illustrating the steps that may be performed in selecting an optimal signal from a photodetector array, in accordance with an embodiment of the present disclosure.

As described above for the embodiments in FIG. 3 and FIG. 4, regardless of whether the selection of the optimal signal from the photodetector array is performed by the processor 120 (as in FIG. 3) or the signal analyzer 150 (as in FIG. 4), a similar method may be employed. For example, FIG. 5a presents a block diagram 180 describing a series of steps that may be used to determine the optimal photodetector signal. The method first determines (block 182) if all of the photodetectors in the photodetector array 32 have been sampled. If unsampled photodetectors remain, the processor 120 or the signal analyzer 150 sends (block 184) a signal to the multiplexor driver 112 to switch and output the signal of the next photodetector (e.g., any of 32A-H) in the photodetector array 32.

Next, the signal from the selected photodetector is acquired (block 186) and rated (i.e. the quality of the signal is assessed) by the processor 120 or the signal analyzer 150. The processor 120 or the signal analyzer 150 may compare (block 188) the newly acquired signal to the previous best signal acquired. If the newly acquired signal is the first signal to be acquired, the newly acquired signal advances to the next step (block 190) and is stored as the new best signal. Otherwise, the new signal and the previous-best signal are compared based upon one or more signal metrics. For example, the two signals may be compared based upon signal magnitude, wherein the strongest signal is determined to be the better quality signal. The comparison may also take noise into account, wherein the signal having the lowest noise may be determine to be the better quality signal (e.g., based upon a comparison of signal-to-noise ratio or the signal noise level of each signal). The comparison may also take into account predetermined acceptable signal range values, wherein only signals falling inside this range may be determined to be quality signals.

If, based upon the chosen metrics for comparison, the newly acquired signal is determined (block 188) to be of better quality that the previous best signal acquired, then the newly acquired signal is stored as the new best signal (block 190). Regardless of the outcome, the method then returns to the beginning and once again determines (block 182) if any unread photodetectors remain. If more photodetectors remain to be sampled, the method repeats blocks 184 through 190 for the remaining photodetectors. Once all photodetectors in the photodetector array 32 have been sampled, then the stored best signal is selected (block 192) as the best signal for the photodetector array 32. In the embodiment of FIG. 3, since the processor 120 may perform a method such as is described by FIG. 5a, the processor 120 may then use the selected best signal for calculation of the physiological characteristics of the patient 104. In the embodiment of FIG. 4, since the signal analyzer 150 may perform a method such as is described by FIG. 5a, the signal analyzer 150 may transmit the selected best signal to the monitor 12B (to eventually arrive at the processor 120) via the signal input line 110.

The scan of the photodetector elements outlined above may be performed continuously, intermittently, or at regular time intervals. In this manner, the processor 120 may be able to take into account changing conditions of the sensor 26 in real-time during calculation of physiological parameters of a patient. That is, the processor 120 may factor in changing conditions of the sensor 26 while processing data received from the sensor 26 without any intentional delays being added to the time required to perform the processing (i.e. in real-time). For example, if a photodetector (e.g., 32A) previously determined to receive the strongest light transmission from the emitter 30 is exposed to ambient light (for instance, due to the sensor 26 becoming loose through movement of the patient 104), the processor 120 may determine that the photodetector 32A has been corrupted in its ability to receive light from the emitter 30. Accordingly, the processor 120 may instruct the multiplexor driver 112 to poll different photodetectors (e.g., 32B or 32C) for the calculation of physiological parameters of the patient 104. For an embodiment of a sensor 26B of FIG. 4, the signal analyzer 150 may play a similar role when selecting the optimal signal to transmit to the monitor 12B, forgoing signals from photodetectors beyond a predetermined threshold in favor of signals that are in acceptable range. Thus, the photodetectors 32A-C of the photodetector array 32 may be scanned in real-time so that the best available received light may consistently be used by the processor 120 for the calculation of physiological parameters of the patient 104.

Figure 5B:
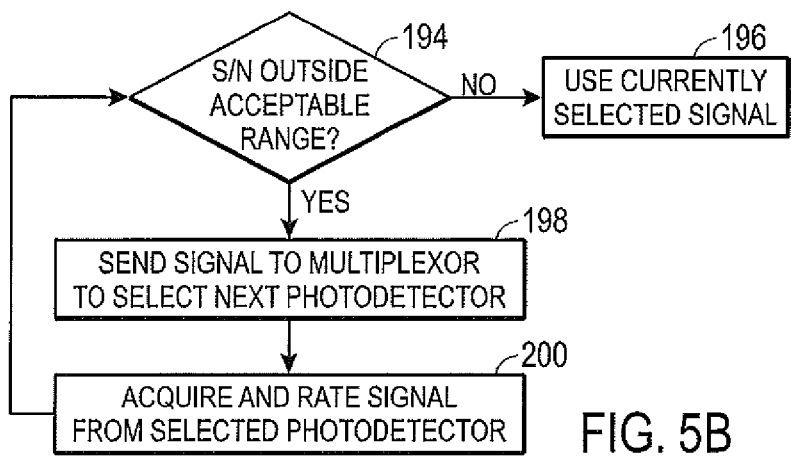
FIG. 5b is a block diagram illustrating the steps that may be performed in a method of maintaining a selection of a photodetector in a photodetector array while its signal remains acceptable, in accordance with an embodiment of the present disclosure.

Alternatively, the processor 120 or the signal analyzer 150 may instead only have the multiplexor 102 select a different photodetector when the quality of the signal from a selected photodetector becomes unacceptable. For example, FIG. 5b presents a block diagram illustrating the steps that may be performed in such an embodiment. Initially, the signal produced by the selected photodetector is analyzed to determine (block 194) if the signal quality is outside of an acceptable range. In the illustrated embodiment, the signal quality is determined based upon the signal-to-noise ratio of the selected photodetector signal. Therefore, if the signal-to-noise ratio of the selected signal is within a predetermined tolerance, then the currently selected signal remains selected and continues to be used (block 196) for the calculation of a physiological parameter of the patient. If, however, the signal-to-noise ratio of the signal is beyond an acceptable tolerance level, the multiplexor 102 may be signaled to select (block 198) a different photodetector from the photodetector array. In some embodiments, the method may cycle through the photodetector array in an ordered, round-robin, or a random fashion. Next, the signal for the newly selected photodetector is acquired (block 200) and rated (e.g., the signal-to-noise ratio is determined). From there, the method repeats, and the signal-to-noise ratio is again compared (block 194) to the acceptable threshold. Accordingly, the method will continue to cycle through the photodetector array until an acceptable photodetector signal is located to be used (block 196) for the calculation of a physiological parameter of the patient.

As previously mentioned, sensor embodiments may incorporate one or more arrays of photodetectors and one or more emitters into the body of a sensor, and that the sensor may be affixed to a flexible substrate so as to allow the sensor to be more form fitting to the body of the patient. Additionally, pulse oximeters typically operate to measure light that has either been transmitted through the tissue of the patient (i.e. transmission mode) or light that has been reflected by the tissue of the patient (i.e. reflectance mode). FIGS. 6-9 illustrate sensor embodiments of both modes and their behavior when affixed to the body of the patient. Such sensors may be similar to those described in U.S. Patent Application No. 20100331640, which is incorporated by reference in its entirety herein for all purposes.

Figure 6:
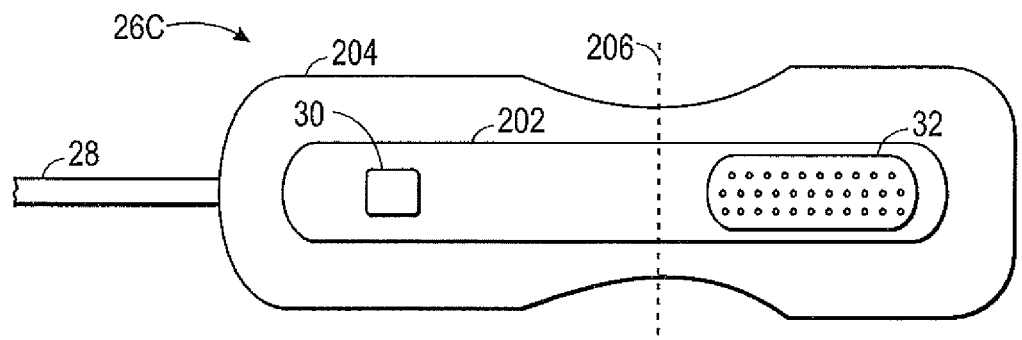
FIG. 6 illustrates a top view of a sensor, in accordance with an embodiment of the present disclosure.

For example, FIG. 6 illustrates an embodiment of a sensor 26C that may include an emitter 30, a photodetector array 32, and a cable 28 for attachment to a monitor 12. The sensor 26C may also include internal components (not shown) as described above for sensors 26A or 26B (e.g., multiplexor 102, encoder 109, signal analyzer 150, and/or multiplexor driver 112). As illustrated, the photodetector array 32 includes a plurality of photodetector elements, e.g., 32 in this example. The photodetector array may, for example, be arranged in a one dimensional line or in a two dimensional pattern as shown. The use of an array of photodetectors 32 may allow for capture of more of the photons emitted by the emitter 30 than a single photodetector, increasing the effectiveness of the sensor 26C. In one embodiment, the emitter 30 and/or the photodetector array 32 may be printed directly onto a flexible substrate 202. The flexible substrate 202 may, for example, be a silicon-based substrate or may be a thermoplastic polymer such as polyethylene terephthalate (PET) foil. Accordingly, the flexible substrate 202 may be a form fitting material that is malleable and maintains its shape once adjusted. In this manner, the flexible substrate 202 may be useful in increasing its tolerance to changing form in response to certain types of motion, such as finger movements, by maintaining a relatively rigid or fixed shape once the sensor has been fitted to the patient. Alternatively, the flexible substrate 202 may be designed to be flexible such that the flexible substrate may maintain contact with a patient 104 when stationary or moving. For example, the flexible substrate 202 may be implemented as part of a neonatal forehead probe and as such, the flexible substrate 202 may remain flexible in response to movements of the patient 104.

As described above, the flexible substrate 202 may be part of the sensor 26C. As such, the flexible substrate 202 may be affixed to a bandage 204 using, for example, an adhesive. In place of (or in addition to) adhesives, the bandage 204 may also include some other affixation element commonly used by one skilled in the art to affix a sensor 26C to a patient 104. Alternatively, the bandage 204 may include, for example, a soft, pliable, low-profile foam material that allows the sensor 26C to remain in place on a patient 104 without the use of adhesives. The bandage 204 may also be flexible, such that any change in shape of the flexible substrate 202 will be accompanied by a corresponding change in shape of the bandage 204. In one embodiment, the flexible substrate 202 and the bandage 204 may be bent around a center axis 206 such that the emitter 30 is brought into proximity with the photodetector array 32. In one embodiment, tissue of a patient 104, (e.g., an ear, a finger, or a toe) may be placed between the emitter 30 and the photodetector array 32. Thus, the sensor 26C may be bent into shape around a given tissue area of a patient 104, and because of the malleable nature of both the flexible substrate 202 and the bandage 204, the photodetector array 32 may conform to patient 104 tissue to maximize the light received from the emitter 30 in a manner described in further detail below.

Figure 7:
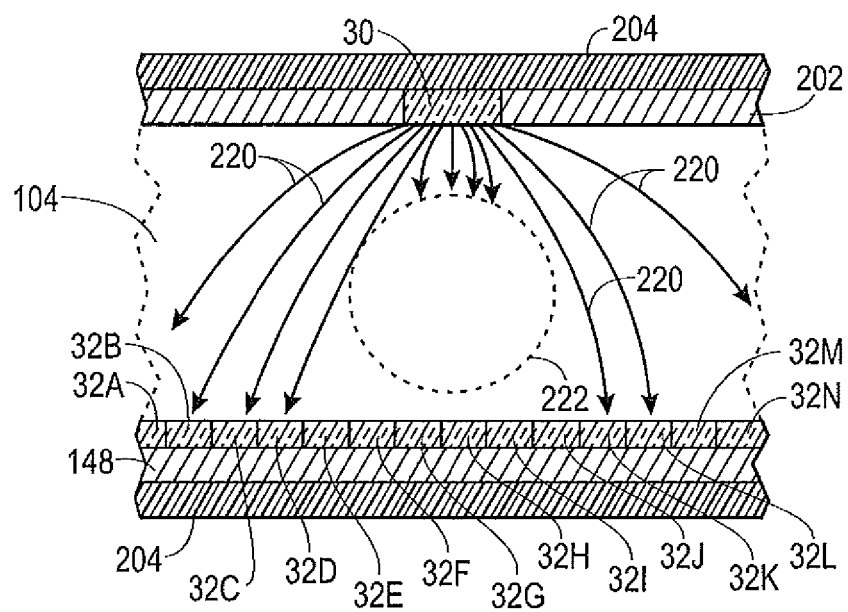
FIG. 7 illustrates a side view of the sensor of FIG. 6, in accordance with an embodiment of the present disclosure.

As mentioned above, when affixed to a patient, the sensor 26C may employ a transmission-mode measurement to determine one or more physiological characterizes of a patient. For example, FIG. 7 illustrates the sensor 26C disposed on the tissue of a patient 104 as set forth above. As may be seen, the emitter 30 may, for example, be positioned above the photodetector elements 32A-N of the photodetector array 32 such that light may pass through the patient 104 via one or more light paths 220. As described above, the emitter 30 may include one or more light emitting diodes (LEDs) that may be used to measure, for example, oxygen saturation, water fractions, hematocrit, or other physiologic parameters of the patient 104. While the illustrated photodetectors 32A-N are depicted in a single line, it should be noted that these elements 32A-N may, for example, be arranged in a two-dimensional array. In operation, light enters the photodetector elements 32A-N after passing through the tissue of the patient 104 via light paths 220. The photodetectors 32A-N may convert the light at a given intensity, which may be directly related to the absorbance and/or reflectance of light in the tissue of the patient 104, into an electrical signal.

However, there may be bone 222 or other constituents in the tissue of the patient 104 that may undesirably absorb and/or scatter light from the emitter 30. In this example, the bone 222 may operate to absorb light attempting to pass through the bone 222 such that given photodetector elements 32F-I may not receive sufficient light to generate an electrical signal such as may be used to calculate the physiologic parameters of the patient 104. However, light may be received at other locations (e.g., at photodetectors 32B-D and/or 32J-K), which may be used by the processor 120 to calculate the physiologic parameters of the patient 117.

Other processing of the signals received at the photodetector 32 may include the determination of which received signals from a location, such as location 32B, 32C, or 32K, should be used to calculate physiological parameters of the patient 104. As described above, light received at certain locations, such as location 202, may be too weak to properly generate a useable signal for calculation of physiological parameters of the patient 104. Accordingly, the processor 120 or signal analyzer 150 may be used to determine which individual photodetectors 32A-N are receiving the strongest light transmission from the emitter 30, for example, using methods similar to those described in FIGS. 5a-b. The one or more photodetector elements 32A-N with the best quality signal may then be chosen, and signals received from the chosen photodetector elements 32A-N may then be utilized to calculate physiological parameters of a patient 104. In this manner, alternate light paths 220 are available to calculate physiological parameters of a patient 104 instead of only a single light path that might otherwise be unusable due to interference. Thus, the proper operation of the sensor 26C may be improved through the use of the photodetector array.

Figure 8:
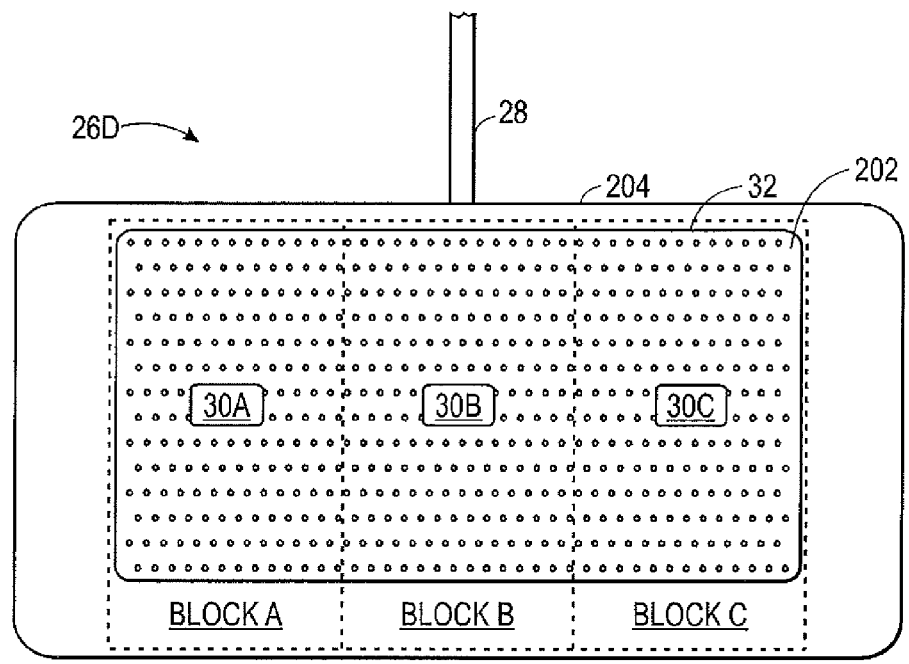
FIG. 8 illustrates a top view of another sensor, in accordance with an embodiment of the present disclosure.

In some embodiments, the photodetector array may be arranged into a series of blocks. Such an embodiment may be useful when it is desirable when different portions of the photodetector array may be used to measure different wavelengths and/or different physiological parameters of the patient. Additionally, dividing the photodetector array into blocks may, for example, allow each portion of the photodetector array to use a common conducting path (i.e. wire) to connect to the multiplexor, thereby allowing a smaller multiplexor to be used for even a large photodetector array. For example, FIG. 8 illustrates a sensor 26D possessing an array of photodetectors 32 divided into blocks (e.g., blocks A-C) that may utilize a reflectance method to receive light signals. Similar to the transmittance type sensor 26C described above, the sensor 26D may include a cable 28 for transmission of signals to and from the sensor 26D, as well as internal sensor components (not shown) previously described (e.g., multiplexor 102, encoder 109, signal analyzer 150, and/or multiplexor driver 112). The sensor 26D may include one or more emitters 30, such as three emitters 30A, 30B, and 30C, positioned adjacent to the a photodetector array 32 on the same side of the tissue of a patient 104. The photodetector array 32 may, for example, surround the emitters 30A-C and may be divided into regions (e.g., Blocks A-C) surrounding the emitters 30A-C. The emitters 30A-C and/or the photodetector array 32 may be printed directly onto a flexible substrate 202 that may be a silicon based substrate or may be a thermoplastic polymer such as polyethylene terephthalate (PET) foil.

As described above, the flexible substrate 202 may be part of the sensor 26D. As such, the flexible substrate 202 may be affixed to a bandage 204 via, for example, an adhesive. The bandage 204 also may include an adhesive or other affixation element that may be used to affix the sensor 26D to a patient 104. In one embodiment, the sensor may be placed on a patient 104, (e.g., on the forehead or finger). The flexible substrate 202 and bandage 204 may be bent into shape around a given tissue area of a patient 104. Due to the nature of both the flexible substrate 202 and the bandage 204, the photodetector array 32 may conform to patient 104 tissue to maximize the light received from the emitters 30.

Furthermore, the use of multiple emitters 30 may be advantageous for the efficiency of the sensor 26D by allowing the measurement of multiple physiological characteristics concurrently. For example, sensor 26D includes three emitters 30A-C, and each of the emitters 30A-C may transmit light of a different wavelength into the tissue of the patient 104. Thus, the first emitter 30A may transmit light of a given wavelength, such as RED light (i.e. around 660 nm) and/or infrared light (i.e. around 900 nm), for the determination of blood oxygen saturation of the patient 104. Additionally, a second emitter 30B may be utilized to determine glucose levels of a patient 104 by transmitting light at a wavelength of approximately 1000 nm. A third emitter 30C may be used to determine hematocrit levels of a patient 104 by transmitting light at a wavelength of approximately 550 nm. Thus, the processor 120 may receive signals from regions of the detector array 32 near to each of these emitters 30A-C to receive data relating to multiple tests on a patient 104 simultaneously. Furthermore, the scanning procedure outlined above in FIG. 5a may be performed for each individual region, such that the best quality signal corresponding to the blood oxygen saturation, glucose level, and hematocrit levels of the patient 104 are selected for the calculation. In such embodiments, multiple multiplexors 102 may be used within the sensor 26D, wherein the blocks of the detector array 32 (e.g., Block A, B, or C) may share a common emitter 30A-C (e.g., corresponding to a particular physiological measurement) and may also share a common multiplexor 102. Alternatively, photodetectors in a common block may share a common conductive path to the same multiplexor 102. For example, a single conductive path may connect all of the photodetectors in Block A to one input of the multiplexor 102, all of the photodetectors in Block B to another input of the multiplexor 102, etc. Accordingly, when the multiplexor 102 selects a channel, the signal on that channel represents a combination of the signals from all of the photodetectors within the selected block.

In another embodiment, the use of multiple emitters 30 may be useful for patients 104 with darkly pigmented skin, since a greater degree of light may be absorbed by the tissue of the patient 104. This may lead to weak signals received at the photodetector array 32. Accordingly, to overcome this potential issue, in an embodiment if a scan of the photodetector array 32 reveals that all photodetectors are receiving weak signals, then the processor 120 may initiate a process whereby two or more adjacent emitters 30A-C may be activated simultaneously to transmit light, for example, at the same wavelength. In this manner, more light may be transmitted into the tissue of the patient 104, which may allow, for example, portions of the photodetector array 32 located between the simultaneously activated emitters 30A-C to receive adequate light for the generation of signals such as may be utilized in the calculation of physiologic parameters of the patient 104. Additionally, other efficiencies with respect to the sensor 26D may be obtained, as described below with respect to FIG. 9.

Figure 9:
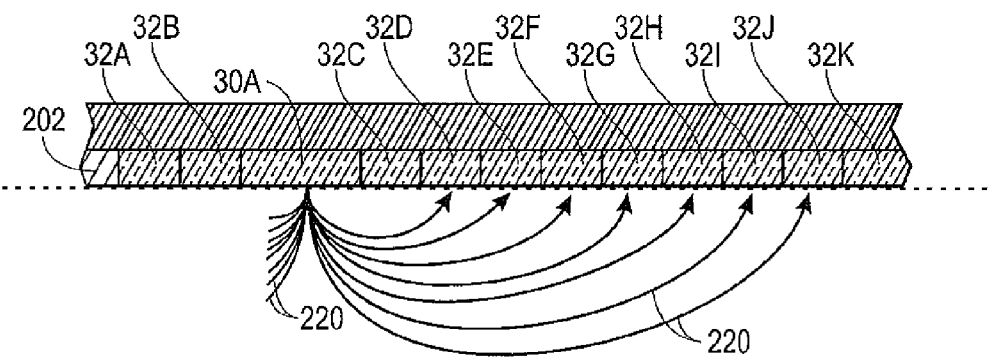
FIG. 9 illustrates a side view of the sensor of FIG. 8, in accordance with an embodiment of the present disclosure.

When affixed to a patient, the sensor 26D may employ a reflectance-type measurement to determine one or more physiological characterizes of a patient. For example, FIG. 9 illustrates a portion of the sensor 26D of FIG. 8 in contact with the tissue of a patient 104. As may be seen, the emitter 30A may, for example, be positioned adjacent to the photodetector elements 32A-K such that light may pass through the patient 104 via one or more light paths 220. The light paths 220 may, for example, begin at emitter 30A and end at photodetector elements 32D-J, respectively. Accordingly, the light path 220 ending at location 32D is shorter than the light path 220 ending at location 32G, which is shorter than the light path 220 ending at location 32J. Additionally, the light path 220 ending at location 32D follows a shallower route than the light path 220 ending at location 32G, which is shallower than the light path 220 ending at location 32J. Light paths 220 that pass through the tissue of the patient 104 at different depths and having different lengths may be advantageous for scanning and selecting signals from the photodetector array 32 at certain locations on the patient 104. That is, as described above, if, for example, bone or other tissue interferes with the light path 220 to a given location (e.g., 32D) such that a given photodetector element (e.g., 32D) may not receive sufficient light to generate an adequate electrical signal for further computation, the processor 120 or the signal analyzer 150 may scan the detector array 32 for signals from other locations (e.g., photodetectors 32G and/or 32J), which may be used by the processor 120 to calculate the physiological parameters of the patient 104.

Additionally, the sensor 26D may be utilized to determine physiological parameters for both adults and infants. In general, adults tend to have thicker skin than infants. Accordingly, it is generally desirable that light paths 220 go deeper into the skin of an adult patient 104 to properly determine the physiological parameters of the adult patient 104 (e.g., light paths 220 in route to photodetectors 32G and/or 32J). In contrast, for infant patents 104 the light paths 220 utilized to calculate physiological parameters may travel a shallower path (e.g., light paths 220 in route to photodetector 32D). By having a plurality of photodetector elements 32A-K, the processor 120 may scan for the best photodetector 32A-F for use with either an adult or an infant patient 104. In this manner, the same sensor 26D may be utilized for both adult and infant patients 104.

What is claimed is:

1. A physiological sensor comprising:
   one or more emitters configured to transmit light into a patient's tissue;
   a photodetector array comprising a plurality of photodetectors configured to receive the transmitted light from the tissue and produce a corresponding respective output signal;
   a multiplexor configured to receive the output signals from the plurality of photodetectors and to output a selected one of the respective output signals; and
   a signal analyzer configured to:
      make a determination regarding a signal quality of the output signals; and
      select one of the output signals based on the signal quality determination for calculation of a physiological parameter of the patient.

2. The sensor as set forth in claim 1, comprising a multiplexor driver configured to supply select signals to the multiplexor to select one of the respective output signals.

3. The sensor as set forth in claim 2, wherein the signal analyzer is further configured to:
   supply control signals to the multiplexor driver; and
   receive the output signals from the multiplexor.

4. The sensor as set forth in claim 3, wherein the signal analyzer, the multiplexor driver, or both, are removably attached to the physiological sensor.

5. The sensor as set forth in claim 3, wherein the signal quality determination is based on signal intensity, signal range, signal noise level, or signal-to-noise ratio, or any combination thereof.

6. The sensor as set forth in claim 1, wherein the one or more emitters and the plurality of photodetectors are coupled to a flexible substrate.

7. The sensor as set forth in claim 1, wherein the one or more photodetectors are grouped into blocks coupled to the multiplexor.

8. The sensor as set forth in claim 7, wherein each block of photodetectors is configured to receive the transmitted light from the patient's tissue.

9. A pulse oximetry monitor comprising:
   a multiplexor driver configured to supply control signals to a multiplexor on a pulse oximetry sensor to select an output signal from a photodetector array of a pulse oximetry sensor; and
   processing circuitry configured to:
      control the multiplexor driver,
      receive the selected output signal from the photodetector array on a pulse oximetry sensor,
      determine if the quality of the received signal is acceptable to perform a calculation of a physiological parameter of a patient and, if it is not, cause the multiplexor driver to supply different control signals to the multiplexor on the pulse oximetry sensor to select different photodetectors in the photodetector array until a photodetector with an acceptable quality signal is determined, and calculate the physiological parameter of the patient based on the received output signal.

10. The pulse oximetry monitor as set forth in claim 9, comprising a pulse oximetry sensor comprising:

one or more emitters configured to transmit light;

an array of photodetectors, each photodetector configured to receive the transmitted light and produce a respective output signal; and a multiplexor configured to receive the output signals from the array of photodetectors and to output a selected output signal.

11. The pulse oximetry monitor as set forth in claim 10, comprising a plurality control lines configured to transmit control signals from the pulse oximetry monitor to the multiplexor of the pulse oximetry sensor to select one of the output signals.

12. The pulse oximetry monitor as set forth in claim 10, wherein the plurality of control lines comprise N control lines to control the pulse oximetry sensor having an array of $2^N$ photodetectors.

13. The pulse oximetry monitor as set forth in claim 9, wherein the quality of the signal output from the multiplexor is determined based upon an analysis of signal intensity, signal range, signal noise level, signal-to-noise ratio, or any combination thereof.

14. A method of choosing a signal from a multiplexed photodetector array of a physiological patient sensor comprising:

selecting and measuring each photodetector signal from the multiplexed photodetector array;

determining a signal quality of each selected photodetector signal;

comparing the signal quality of each selected photodetector signal to a threshold value; and choosing a photodetector signal based upon the comparison.

15. The method as set forth in claim 14, wherein determining the signal quality of each selected photodetector signal comprises analyzing the signal quality of each selected photodetector based on signal intensity, signal range, signal noise level, or signal-to-noise ratio, or any combination thereof.

16. The method as set forth in claim 14, comprising remaining with the chosen photodetector signal selected until the signal quality of the chosen photodetector signal is below the threshold value.

17. The method as set forth in claim 14, wherein the threshold value is a lower limit for the signal quality, an upper limit for the signal quality, or the signal quality of a measured photodetector signal.

* * * * *